United States Patent [19]

Sirrenberg et al.

[11] 4,348,394
[45] Sep. 7, 1982

[54] COMBATING PESTS WITH SUBSTITUTED 3,6-DIPHENYL-3,4-DIHYDRO-2H-1,3,5-OXADIAZINE-2,4-DIONES

[75] Inventors: Wilhelm Sirrenberg, Sprockhoevel; Erich Klauke, Odenthal; Ingeborg Hammann; Ingomar Krehan, both of Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 219,751

[22] Filed: Dec. 22, 1980

Related U.S. Application Data

[63] Continuation of Ser. No. 115,854, Jan. 28, 1980, abandoned.

[30] Foreign Application Priority Data

Feb. 14, 1979 [DE] Fed. Rep. of Germany ....... 2905687

[51] Int. Cl.³ .................... C07D 273/04; A01N 9/20
[52] U.S. Cl. ................... 424/248.57; 544/67; 260/453 AR
[58] Field of Search ...................... 544/67; 424/248.57

[56] References Cited

U.S. PATENT DOCUMENTS 4,150,158  4/1979  Huff ................................. 424/248.57
4,200,653  4/1980  Huff et al. .......................... 424/322

FOREIGN PATENT DOCUMENTS 2732115  1/1978  Fed. Rep. of Germany ........ 544/67
7430110  4/1976  France ................................. 544/67

Primary Examiner—Joseph Paul Brust
Attorney, Agent, or Firm—Sprung, Horn, Kramer & Woods

[57] ABSTRACT

An oxidiazine derivative of the formula

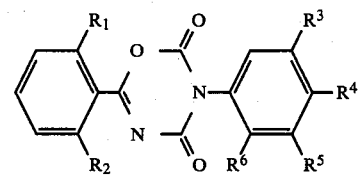

in which
$R^1$ represents halogen or alkyl,
$R^2$ represents hydrogen or halogen,
$R^3$, $R^5$ and $R^6$ are selected independently of one another and each represent hydrogen, halogen, alkyl or halogenoalkyl and
$R^4$ represents halogenoalkyl, halogenoalkoxy, halogenoalkylthio or tert.-alkyl, or $R^4$, together with $R^3$, represents dioxahalogenoalkanediyl or, in the case where at least one of the radicals $R^3$, $R^5$ and $R^6$ represents halogenoalkyl, $R^4$ may alternatively represent hydrogen or halogen, or in the case where $R^1$ represents chlorine and at the same time $R^2$ represents fluorine, $R^4$ may alternatively represent halogen or alkoxy, which possesses arthropodicidal and nematicidal properties.

8 Claims, No Drawings

COMBATING PESTS WITH SUBSTITUTED 3,6-DIPHENYL-3,4-DIHYDRO-2H-1,3,5-OXADIAZINE-2,4-DIONES

This is a continuation of application Ser. No. 115,854, filed Jan. 28, 1980, now abandoned.

The invention relates to certain new oxadiazine derivatives, to a process for their preparation and to their use as agents for combating pests, especially as insecticides.

It is already known that certain oxadiazine derivatives, for example 3-(3-chlorophenyl)-6-(2,6-difluorophenyl)-3,4-dihydro-2H-1,3,5-oxadiazine-2,4-dione, have an insecticidal action (see DE-OS (German Published Specification) No. 2,732,115). However, the action of these compounds is not always satisfactory, especially in the case of low concentrations of active compound and when small amounts are used.

The present invention now provides, as new compounds, the oxadiazine derivatives of the general formula (I)

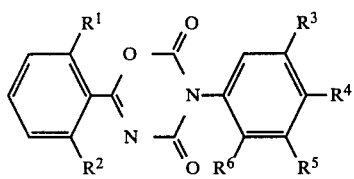

in which
R$^1$ represents halogen or alkyl,
R$_2$ represents hydrogen or halogen,
R$^3$, R$^5$ and R$^6$ are selected independently of one another and each represent hydrogen, halogen, alkyl or halogeno-alkyl and
R$^4$ represents halogenoalkyl, halogenoalkoxy, halogenoalkylthio or tert.-alkyl, or R$^4$ together with R$^3$, represents dioxahalogeno-alkanediyl, or in the case where at least one of the radicals R$^3$, R$^5$ and R$^6$ represents halogenalkyl, R$^4$ may alternatively represent hydrogen or halogen, or in the case where R$^1$ represents chlorine and at the same time R$^2$ represents fluorine, R$^4$ may alternatively represent halogen or alkoxy.

Surprisingly, the oxadiazine derivatives of the formula (I) have been found to exhibit a considerably higher activity as agents for combating pests, especially a higher insecticidal action, than compounds of analogous structure and with the same type of action which are known from the state of the art.

Preferred compounds of the formula (I) are those in which
R$^1$ represents fluorine, chlorine, bromine, iodine, methyl or ethyl.
R$^2$ represents hydrogen, fluorine, chlorine, bromine or iodine.
R$^3$, R$^5$ and R$^6$ are selected independently of one another and each represent hydrogen, chlorine, methyl or trifluoromethyl and
R$^4$ represents tert.-butyl, tert.-pentyl, difluoromethyl, trifluoromethyl, chlorodifluoromethyl, difluoromethoxy, trifluoromethoxy, chlorodifluoromethoxy, 1,1,2,2-tetrafluoroethoxy, 2-chloro-1,1,2-trifluoroethoxy, trifluoromethylthio or chlorodifluoromethylthio, or R$^4$, together with R$^3$, represents 2,2,4,4-tetrafluoro-1,3-dioxabutane-1,4-diyl, 2,2,3-trifluoro-1,4-dioxabutane-1,4-diyl, 2-chloro-2,3,3-trifluoro-1,4-dioxabutane-1,4-diyl, 2,2-difluoro-1,4-dioxabutane-1,4-diyl or 2,2-difluoro-1,3-dioxapropane-1,3-diyl, or in the case where at least one of the radicals R$^3$, R$^5$ and R$^6$ represents trifluoromethyl, R$^4$ may alternatively represent hydrogen or chlorine, or in the case where R$^1$ represents chlorine and at the same time R$^2$ represents fluorine, R$^4$ may alternatively represent chlorine, methoxy, ethoxy, propoxy or butoxy.

The invention also provides a process for the preparation of an oxidiazine derivative of the formula (I) in which a substituted benzoyl isocyanate of the general formula (II)

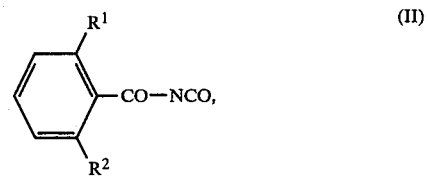

in which R$^1$ and R$^2$ have the meanings indicated above, is reacted with a substituted phenyl isocyanate of the general formula (III)

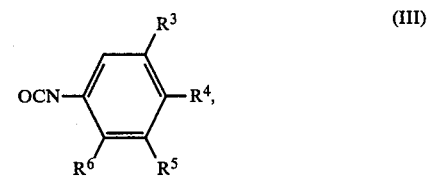

in which R$^3$, R$^4$, R$^5$ and R$^6$ have the meanings indicated above, if appropriate using an inert diluent.

If, for example, 2-chlorobenzoyl isocyanate and 4-trifluoromethoxyphenyl isocyanate are used as starting materials the reaction of these compounds can be outlined by the following equation:

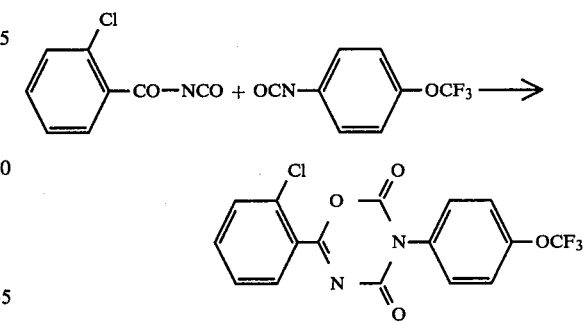

In the formulae (II) and (III) provide a definition of the starting substances to be used. Preferably in these formulae, R$^1$ to R$^6$ have those meanings which have been mentioned as preferred in the case of the definition of R$^1$ to R$^6$ in the formula (I).

The benozyl isocyanates of the formula (II) to be used as starting materials are known, and they can be prepared by known processes. They are obtained, for example, by reacting substituted benzoic acid amides with oxalyl chloride at temperatures between $-20°$ C. and $+100°$ C., if appropriate using a diluent, for example 1,2-dichloroethane (see DE-OS (German Published Specification) No. 2,732,115). Examples of the benzoyl isocyanates of the formula (II) which may be mentioned are: 2-fluoro-, 2-chloro-, 2-bromo- and 2-iodo-benzoyl isocyanate and 2,6-difluoro-, 2,6-dichloro- and 2-chloro-6-fluoro-benozyl isocyanate.

The substituted phenyl isocyanates of the formula (III) also to be used as starting materials are likewise known, or they can be prepared by known processes (see for example, J. Org. Chem. 29 (1964), 1-11; U.S. Pat. No. 4,103,022 and U.S. Pat. No. 4,139,636 Examples of the substituted phenyl isocyanates of the formula (III) which may be mentioned are: 2-chloro-, 3-chloro- and 4-chloro-phenyl isocyanate, 3,4-dichloro-, 2,4-dichloro-, 3,5-dichloro- and 2-methyl-4-chloro-phenyl isocyanate, 4-tert.-butyl- and 4-tert.-pentyl-phenyl isocyanate, 4-methoxy-, 4-ethoxy-, 4-propoxy- and 4-butoxy-phenyl isocyanate, 3-difluoromethyl- and 4-difluoromethyl-phenyl isocyanate, 3-trifluoromethyl- and 4-trifluoromethyl-phenyl isocyanate, 3-chlorodifluoromethyl- and 4-chlorodifluoromethyl-phenyl isocyanate, 3,5-bis-trifluoromethyl-phenyl isocyanate, 3-chloro-4-trifluoromethyl-, 2-chloro-4-trifluoromethyl-, 4-chloro-2-trifluoromethyl-, 2-chloro-5-trifluoromethyl-, 2-chloro-4-chlorodifluoromethyl- and 3-chloro-4-chlorodifluoromethyl-phenyl isocyanate, 4-difluoromethoxy- and 3-chloro-4-difluoromethoxy-phenyl isocyanate, 4-trifluoromethoxy- and 3-chloro-4-trifluoromethoxy-phenyl isocyanate, 4-chlorodifluoromethoxy- and 3-chloro-4-chlorodifluoromethoxy-phenyl isocyanate, 4-(1,1,2,2-tetrafluoromethoxy)- and 4-(2-chloro-1,1,2-trifluoroethoxy)-phenyl isocyanate, 4-trifluoromethylthio-, 4-chlorodifluoromethylthio-, 3-chloro-4-trifluoromethylthio- and 3-chloro-4-chlorodifluoromethylthio-phenyl isocyanate and 6-isocyanato-2,2,4,4-tetrafluoro-benzo-1,3-dioxine.

If appropriate, the process for the preparation of the new oxadiazine derivatives is carried out using an inert diluent. Possible diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile. In general, however, the use of diluents is not necessary.

The reaction temperature can be varied within a substantial range. In general, the reaction is carried out at from 20° to 200° C., preferably at from 50° to 150° C. The process according to the invention is in general carried out under normal pressure.

The starting materials are usually employed in equimolar amounts for carrying out the process according to the invention. An excess of one or other of the reactants brings no substantial advantages. The reactants are mixed, if appropriate in a suitable diluent, and the mixture is stirred at the required temperature for several hours. After cooling, the products, which are obtained in solid form, are triturated with a non-polar diluent, for example cyclohexane, and separated off by filtration. The melting point is used for their characterization.

The new oxidiazine derivatives are distinguished by an outstanding activity in combating pests, in particular by an insecticidal activity. They are active against insects which are harmful to plants, against pests harmful to health and pests of stored products and against ectoparasites. Some of the new compounds also have a fungicidal action. The compounds according to the invention can thus successfully be used as agents for combating pests in plant protection, in the hygiene sector, in the protection of stored products and in the veterinary field (for the combating of both endoparasites and ectoparasites).

The active compounds are well tolerated by plants, have a favorable level of toxicity to warm-blooded animals, and can be used for combating arthropod pests, especially insects or acarids, or nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locuta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Ericsoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichloplusia ni, Carpocapsa pomonella,* Pieris spp., Chilo spp., *Pyrausta nubi-*

*lalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineate, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., Monomorium pharacnis and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Cestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichlodorus spp.

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms (an be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) or nematodes, which comprises applying to the arthropods or nematodes, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects which comprises applying to said animals a compound according to the present invention, in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects by the application to said animals of a compound according to the present invention, in admixture with a diluent or carrier.

The preparation of the novel compounds is illustrated in the following example:

EXAMPLE 1

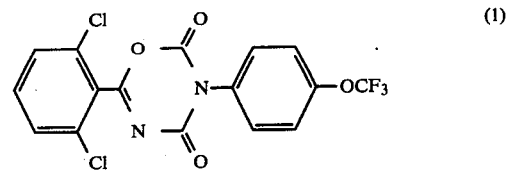

6.48 g (0.03 mol) of 2,6-dichlorobenzoyl isocyanate and 6.09 g (0.03 mol) of 4-trifluoromethoxyphenyl isocyanate were heated to 100°–110° C. for 16 hours with exclusion of moisture. After cooling the mixture, the reaction product, which was obtained as a compact crystal mass, was triturated carefully with cyclohexane, filtered off, washed once with cyclohexane and then once with petroleum ether and then dried. 12.2 g (97% of theory) of the crystalline compound with a melting point of 208° C. were obtained.

The following compounds of the general formula

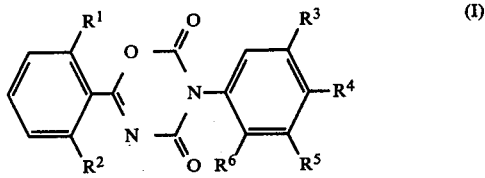

were prepared analogously, without attempting to optimize the yields:

| Compound No. | $R^1$ | $R^2$ | $R^3$ | $R^4$ | $R^5$ | $R^6$ | Yield (% of theory) | Melting point (°C.) |
|---|---|---|---|---|---|---|---|---|
| 2 | Cl | Cl | H | $SCF_3$ | H | H | 77.6 | 200 |
| 3 | Cl | Cl | \multicolumn{2}{c}{$-CF_2-O-CF_2-O-$} | H | H | 26.8 | 186 |
| 4 | Cl | Cl | H | $OCF_2CHF_2$ | H | H | 100 | 210 |
| 5 | Cl | Cl | H | $CHF_2$ | H | H | 75.5 | 213 |
| 6 | Cl | Cl | Cl | $SCF_3$ | H | H | 95.5 | 186 |
| 7 | Cl | Cl | Cl | $SCF_2Cl$ | H | H | 77 | 172 |
| 8 | Cl | Cl | Cl | $CF_2Cl$ | H | H | 84.5 | 208 |
| 9 | Cl | Cl | Cl | $OCF_3$ | H | H | 26.5 | 180 |
| 10 | Cl | Cl | $CF_3$ | H | H | H | 50.5 | 177 |
| 11 | Cl | Cl | Cl | $OCF_2Cl$ | H | H | 91.5 | 173 |
| 12 | Cl | Cl | H | $CF_2Cl$ | H | H | 89.5 | 214 |
| 13 | Cl | Cl | H | $OCF_2Cl$ | H | H | 92.5 | 198 |
| 14 | Cl | Cl | $CF_3$ | H | $CF_3$ | H | 96.5 | 203 |
| 15 | Cl | H | H | $OCF_3$ | H | H | 92.5 | 205 |
| 16 | Cl | H | H | $SCF_3$ | H | H | 80 | 196 |
| 17 | Cl | H | \multicolumn{2}{c}{$-CF_2-O-CF_2-O-$} | H | H | 69.5 | 197 |
| 18 | Cl | H | Cl | $OCHF_2$ | H | H | 51 | 172 |
| 19 | Cl | H | H | $OCF_2-CHF_2$ | H | H | 86.5 | 203 |
| 20 | Cl | H | H | $CHF_2$ | H | H | 78 | 200 |
| 21 | Cl | H | Cl | $SCF_3$ | H | H | 37.9 | 153 |
| 22 | Cl | H | Cl | $SCF_2Cl$ | H | H | 57.5 | 153 |
| 23 | Cl | H | Cl | $CF_2Cl$ | H | H | 26.5 | 184 |
| 24 | Cl | H | Cl | $OCF_3$ | H | H | 72.5 | 167 |
| 25 | Cl | H | Cl | $OCF_2Cl$ | H | H | 71 | 155 |
| 26 | Cl | H | H | $CF_2Cl$ | H | H | 83 | 215 |
| 27 | Cl | H | H | $OCHF_2$ | H | H | 91 | 195 |
| 28 | Cl | H | H | $OCF_2Cl$ | H | H | 83.5 | 198 |
| 29 | Cl | H | H | $SCF_2Cl$ | H | H | 78 | 187 |
| 30 | Cl | H | $CF_3$ | H | $CF_3$ | H | 50 | 188 |
| 31 | Cl | H | $CF_3$ | H | H | Cl | 28.5 | 179 |
| 32 | Cl | H | H | Cl | H | $CF_3$ | 33 | 166 |
| 33 | Cl | H | H | $CF_3$ | H | H | 81.5 | 213 |
| 34 | Cl | H | Cl | $CF_3$ | H | H | 76.5 | 194 |

-continued

| Compound No. | $R^1$ | $R^2$ | $R^3$ | $R^4$ | $R^5$ | $R^6$ | Yield (% of theory) | Melting point (°C.) |
|---|---|---|---|---|---|---|---|---|
| 35 | Cl | H | H | $CF_3$ | H | Cl | 31 | 174 |
| 36 | Cl | H | H | $CF_2Cl$ | H | Cl | 28.5 | 163 |
| 37 | Cl | F | H | $OCF_3$ | H | H | 63 | 199 |
| 38 | Cl | F | H | $SCF_3$ | H | H | 60.5 | 189 |
| 39 | Cl | F | \multicolumn{2}{c}{$-CF_2-O-CF_2-O-$} | H | H | 35.5 | 164 |
| 40 | Cl | F | Cl | $OCHF_2$ | H | H | 34.5 | 173 |
| 41 | Cl | F | H | $OCF_2-CHF_2$ | H | H | 85.5 | 216 |
| 42 | Cl | F | H | $CHF_2$ | H | H | 100 | 212 |
| 43 | Cl | F | Cl | $SCF_3$ | H | H | 17.5 | 162 |
| 44 | Cl | F | Cl | $SCF_2Cl$ | H | H | 23 | 141 |
| 45 | Cl | F | Cl | $CF_2Cl$ | H | H | 44.5 | 193 |
| 46 | Cl | F | Cl | $OCF_3$ | H | H | 26 | 175 |
| 47 | Cl | F | H | Cl | H | H | 52 | 191 |
| 48 | Cl | F | Cl | Cl | H | H | 51.5 | 177 |
| 49 | Cl | F | H | $OCH_3$ | H | H | 66.5 | 172 |
| 50 | Cl | F | H | $C(CH_3)_3$ | H | H | 36.5 | 163 |
| 51 | Cl | F | $CF_3$ | H | H | H | 25.5 | 134 |
| 52 | Cl | F | Cl | $OCF_2Cl$ | H | H | 55 | 173 |
| 53 | Cl | F | H | $CF_2Cl$ | H | H | 57 | 217 |
| 54 | Cl | F | H | $OCHF_2$ | H | H | 73 | 182 |
| 55 | Cl | F | H | $OCF_2Cl$ | H | H | 87.5 | 202 |
| 56 | Cl | F | H | $SCF_2Cl$ | H | H | 42.5 | 186 |
| 57 | Cl | F | $CF_3$ | H | $CF_3$ | H | 30.5 | 191 |
| 58 | Cl | F | H | Cl | H | $CH_3$ | 31 | 179 |
| 59 | Cl | F | H | $CF_3$ | H | H | 63 | 221 |
| 60 | Cl | F | Cl | $CF_3$ | H | H | 51.5 | 202 |
| 61 | Cl | F | H | $CF_3$ | H | Cl | 21 | 185 |
| 62 | Cl | F | H | $CF_2Cl$ | H | Cl | 18 | 196 |
| 63 | F | F | H | $OCF_3$ | H | H | 67 | 194 |
| 64 | F | F | H | $SCF_3$ | H | H | 64.5 | 190 |
| 65 | F | F | \multicolumn{2}{c}{$-CF_2-O-CF_2-O-$} | H | H | 75 | 178 |
| 66 | F | F | H | $OCF_2-CHF_2$ | H | H | 82 | 201 |
| 67 | F | F | H | $CHF_2$ | H | H | 68 | 203 |
| 68 | F | F | Cl | $SCF_3$ | H | H | 52.5 | 171 |
| 69 | F | F | Cl | $SCF_2Cl$ | H | H | 50.5 | 160 |
| 70 | F | F | Cl | $OCF_3$ | H | H | 76 | 190 |
| 71 | F | F | $CF_3$ | H | H | H | 58 | 146 |
| 72 | F | F | Cl | $OCF_2Cl$ | H | H | 80 | 180 |
| 73 | F | F | H | $CF_2Cl$ | H | H | 76 | 212 |
| 74 | F | F | H | $OCHF_2$ | H | H | 92 | 205 |
| 75 | F | F | H | $OCF_2Cl$ | H | H | 77 | 184 |
| 76 | F | F | H | $SCF_2Cl$ | H | H | 67.5 | 182 |
| 77 | F | F | $CF_3$ | H | $CF_3$ | H | 45.5 | 175 |
| 78 | F | F | $CF_3$ | H | H | Cl | 59.5 | 185 |
| 79 | F | F | H | Cl | H | $CF_3$ | 35 | 166 |
| 80 | F | F | H | $CF_3$ | H | H | 64.5 | 230 (decomp.) |
| 80 | F | F | Cl | $CF_3$ | H | H | 53 | 204 |
| 82 | F | F | H | $CF_3$ | H | Cl | 22 | 181 |
| 83 | F | F | H | $CF_2Cl$ | H | Cl | 22.5 | 184 |
| 84 | Br | H | H | $OCF_3$ | H | H | 83 | 194 |
| 85 | Br | H | H | $SCF_3$ | H | H | 94 | 194 |
| 86 | Br | H | \multicolumn{2}{c}{$-CF_2-O-CF_2-O-$} | H | H | 86 | 192 |
| 87 | Br | H | H | $OCF_2CHF_2$ | H | H | 92 | 195 |
| 88 | Br | H | H | $CHF_2$ | H | H | 91 | 198 |
| 89 | Br | H | Cl | $SCF_3$ | H | H | 62.5 | 161 |
| 90 | Br | H | Cl | $SCF_2Cl$ | H | H | 62 | 146 |
| 91 | Br | H | Cl | $OCF_3$ | H | H | 85 | 161 |
| 92 | Br | H | $CF_3$ | H | H | H | 85 | 162 |
| 93 | Br | H | Cl | $OCF_2Cl$ | H | H | 68.5 | 172 |
| 94 | Br | H | H | $CF_2Cl$ | H | H | 73.5 | 214 |
| 95 | Br | H | H | $OCHF_2$ | H | H | 75 | 186 |
| 96 | Br | H | H | $OCF_2Cl$ | H | H | 75 | 195 |
| 97 | Br | H | H | $SCF_2Cl$ | H | H | 66 | 181 |
| 98 | Br | H | $CF_3$ | H | H | Cl | 36.5 | 185 |
| 99 | Br | H | H | $CF_3$ | H | H | 71 | 211 |
| 100 | Br | H | Cl | $CF_3$ | H | H | 65.5 | 192 |
| 101 | Br | H | H | $CF_3$ | H | Cl | 24.5 | 184 |
| 102 | Br | H | H | $CF_2Cl$ | H | Cl | 29 | 178 |
| 103 | I | H | H | $OCF_3$ | H | H | 95 | 174 |
| 104 | I | H | H | $SCF_3$ | H | H | 88.5 | 177 |
| 105 | I | H | \multicolumn{2}{c}{$-CF_2-O-CF_2-O-$} | H | H | 91 | 184 |
| 106 | I | H | H | $OCF_2-CHF_2$ | H | H | 82.5 | 187 |
| 107 | I | H | H | $CHF_2$ | H | H | 61 | 189 |
| 108 | I | H | Cl | $SCF_3$ | H | H | 80.5 | 189 |
| 109 | I | H | Cl | $SCF_2Cl$ | H | H | 87 | 168 |
| 110 | I | H | Cl | $CF_2Cl$ | H | H | 91.5 | 186 |
| 111 | I | H | Cl | $OCF_3$ | H | H | 85 | 189 |
| 112 | I | H | $CF_3$ | H | H | H | 91.5 | 170 |

-continued

| Compound No. | $R^1$ | $R^2$ | $R^3$ | $R^4$ | $R^5$ | $R^6$ | Yield (% of theory) | Melting point (°C) |
|---|---|---|---|---|---|---|---|---|
| 113 | I | H | Cl | $OCF_2Cl$ | H | H | 77.5 | 173 |
| 114 | I | H | H | $CF_2Cl$ | H | H | 69 | 202 |
| 115 | I | H | H | $OCHF_2$ | H | H | 81.5 | 152 |
| 116 | I | H | H | $OCF_2Cl$ | H | H | 72 | 180 |
| 117 | I | H | H | $SCF_2Cl$ | H | H | 57 | 162 |
| 118 | I | H | $CF_3$ | H | $CF_3$ | H | 72.5 | 194 |
| 119 | I | H | $CF_3$ | H | H | Cl | 48.5 | 178 |
| 120 | I | H | H | Cl | H | $CF_3$ | 28 | 141 |
| 121 | I | H | H | $CF_3$ | H | H | 70.5 | 192 |
| 122 | I | H | Cl | $CF_3$ | H | H | 75 | 194 |
| 123 | $CH_3$ | H | H | $OCF_3$ | H | H | 87.5 | 211 |
| 124 | $CH_3$ | H | H | $SCF_3$ | H | H | 81.5 | 203 |
| 125 | $CH_3$ | H | Cl | $SCF_3$ | H | H | 83.5 | 157 |
| 126 | $CH_3$ | H | Cl | $OCF_3$ | H | H | 79 | 170 |
| 127 | $CH_3$ | H | Cl | $OCF_2Cl$ | H | H | 68.5 | 162 |
| 128 | $CH_3$ | H | H | $CF_2Cl$ | H | H | 65.5 | 216 |
| 129 | $CH_3$ | H | H | $OCHF_2$ | H | H | 74.5 | 179 |
| 130 | $CH_3$ | H | H | $OCF_2Cl$ | H | H | 73.5 | 204 |
| 131 | $CH_3$ | H | H | $SCF_2Cl$ | H | H | 69 | 191 |
| 132 | $CH_3$ | H | H | $CF_3$ | H | H | 38.5 | 179 |
| 133 | $CH_3$ | H | H | $CF_3$ | H | Cl | 41.5 | 180 |
| 134 | $CH_3$ | H | H | $CF_2Cl$ | H | Cl | 38.5 | 147 |
| 135 | $C_2H_5$ | H | H | $OCF_3$ | H | H | 21 | 145 |
| 136 | $C_2H_5$ | H | H | $SCF_3$ | H | H | 8.5 | 140 |
| 137 | $C_2H_5$ | H | $CF_3$ | H | H | H | 17.5 | 132 |
| 138 | $C_2H_5$ | H | Cl | $OCF_2Cl$ | H | H | 15 | 145 |
| 139 | $C_2H_5$ | H | H | $CF_2Cl$ | H | H | 19.5 | 183 |
| 140 | $C_2H_5$ | H | H | $OCHF_2$ | H | H | 19.5 | 164 |
| 141 | $C_2H_5$ | H | H | $OCF_2Cl$ | H | H | 20 | 143 |
| 142 | F | H | H | $OCF_3$ | H | H | 84 | 213 |
| 143 | F | H | H | $SCF_3$ | H | H | 63.5 | 197 |
| 144 | F | H | \multicolumn{2}{c}{$-CF_2-O-CF_2-O-$} | H | H | 95.5 | 189 |
| 145 | F | H | H | $OCF_2-CHF_2$ | H | H | 82 | 207 |
| 146 | F | H | H | $CHF_2$ | H | H | 74.5 | 218 |
| 147 | F | H | Cl | $SCF_3$ | H | H | 75.5 | 167 |
| 148 | F | H | Cl | $SCF_2Cl$ | H | H | 68.5 | 168 |
| 149 | F | H | Cl | $OCF_3$ | H | H | 83 | 178 |
| 150 | F | H | $CF_3$ | H | H | H | 65 | 142 |
| 151 | F | H | H | $CF_2Cl$ | H | H | 69 | 216 |
| 152 | F | H | H | $OCF_2Cl$ | H | H | 92 | 203 |
| 153 | F | H | H | $SCF_2Cl$ | H | H | 85 | 202 |
| 154 | F | H | $CF_3$ | H | $CF_3$ | H | 85.5 | 181 |
| 155 | F | H | $CF_3$ | H | H | Cl | 53 | 110 |
| 156 | F | H | H | $CF_3$ | H | H | 89 | 249 (decomp.) |

The pesticidal activity of the compounds of this invention is illustrated by the following examples wherein the compounds according to the present invention are each identified by the number (given in brackets) from Example 1:

EXAMPLE 2

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into a preparation of active compound and were infested with caterpillars of the diamond-back moth (*Plutella maculipennis*), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds showed a superior activity compared to the prior art: (1), (2), (16), (17), (18), (19), (21), (22), (23), (24), (37), (38), (39), (41), (43), (44) (45) and (46).

EXAMPLE 3

Laphygma test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all of the caterpillars had been killed whereas 0% indicated that none of the caterpillars had been killed.

In this test, for example, the following compound showed a superior activity compared to the prior art: (15).

EXAMPLE 4

Mosquito larvae test

Test insects: *Aedes aegypti* larvae
Solvent: 99 parts by weight of acetone
Emulsifier: 1 part by weight of benzylhydroxydiphenyl polyglycol ether To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% meant that all of the larvae were killed. 0% meant that none of the larvae were killed.

In this test, for example, the following compounds showed a superior action compared to the prior art: (37), (38) and (46).

EXAMPLE 5

Test with *Lucilia cuprina* res. larvae

Solvent: 35 parts by weight of ethylene polyglycol monomethyl ether
Emulsifier: 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approx. 2 ml of horse muscle and 0.5 ml of the preparation of active compound. After 24 hours, the degree of destruction in % was determined.

In this test, for example, the following compounds showed a superior action compared to the prior art: (15), (16), (37) and (41).

It will be appreciated that the instant specification and examples are set forth by way of illustration and not limitation, and that various modifications and changes may be made without departing from the spirit and scope of the present invention.

What is claimed is:

1. An oxadiazine derivative of the formula

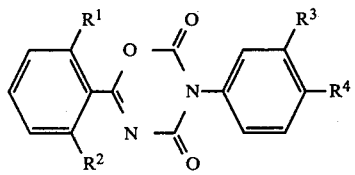

in which
$R^1$ represents halogen, methyl or ethyl,
$R^2$ represents hydrogen or halogen,
$R^3$ represents hydrogen or halogen,
$R^4$ represents halogenomethoxy, halogenoethoxy or halogenomethylthio, or
$R^4$ together with $R^3$ represents dioxahalogenobutanediyl.

2. A compound according to claim 1, in which such compound is 3-(4-trifluoromethoxyphenyl)-6-(2,6-dichlorophenyl)-3,4-dihydro-2H-1,3,5-oxadiazine-2,4-dione of the formula

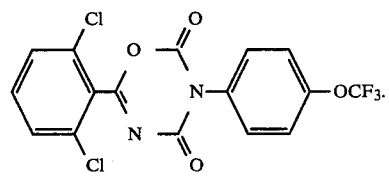

3. A compound according to claim 1, in which such compound is 3-(3-chloro-4-trifluoromethoxyphenyl)-6-(2-chlorophenyl)-3,4-dihydro-2H-1,3,5-oxadiazone-2,4-dione of the formula

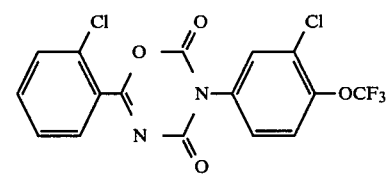

4. A compound according to claim 1, in which such compound is 3-(4-trifluoromethylmercaptophenyl)-6-(2-chlorophenyl)-3,4-dihydro-2H-1,3,5-oxadiazine-2,4-dione of the formula

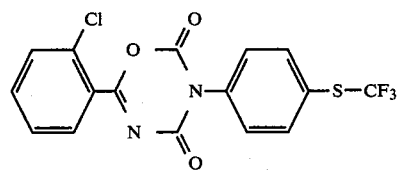

5. A compound according to claim 1, in which such compound is 3-(3-chloro-4-trifluoromethoxyphenyl)-6-(2,6-difluorophenyl)-3,4-dihydro-2H-1,3,5-oxadiazine-2,4-dione of the formula

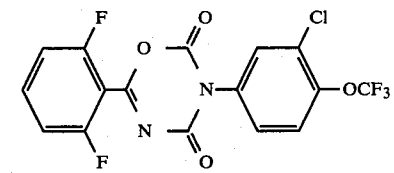

6. An arthropodicidal or nematicidal composition containing as active ingredient an arthropodicidally or nematicidally effective amount of a compound according to claim 1 in admixture with a diluent.

7. A method of combating arthropods or nematodes which comprises applying to the arthropods or nematodes, or to a habitat thereof, an arthropodicidally or nematicidally effective amount of a compound according to claim 1.

8. The method according to claim 7, in which said compound is 3-(4-trifluoromethoxyphenyl)-6-(2,6-dichlorophenyl)-3,4-dihydro-2H-1,3,5-oxadiazine-2,4-dione, 3-(3-chloro-4-trifluoromethoxyphenyl)-6-(2-chlorophenyl)-3,4-dihydro-2H-1,3,5-oxadiazine-2,4-dione, 3-(4-trifluoromethylmercaptophenyl)-6-(2-chlorophenyl)-3,4-dihydro-2H-1,3,5-oxadiazine-2,4-dione, and 3-(3-chloro-4-trifluoromethoxyphenyl)-6-(2,6-difluorophenyl)-3,4-dihydro-2H-1,3,5-oxadiazine-2,4-dione.

* * * * *